United States Patent [19]

Heyl et al.

[11] Patent Number: 5,431,879

[45] Date of Patent: Jul. 11, 1995

[54] METHOD AND CONTAINER FOR STERILIZING AND DISINFECTING

[75] Inventors: Barbara L. Heyl, Atlanta; Lynn C. Winterton, Roswell; Kai C. Su, Alpharetta; Jack C. White, Stone Mountain; William M. Hung, Alpharetta, all of Ga.

[73] Assignee: Ciba-Geigy Corporation, Ardsley, N.Y.

[21] Appl. No.: 283,906

[22] Filed: Aug. 3, 1994

Related U.S. Application Data

[63] Continuation of Ser. No. 877,706, May 4, 1992, abandoned, which is a continuation-in-part of Ser. No. 857,481, Mar. 25, 1992, abandoned, which is a continuation-in-part of Ser. No. 791,248, Nov. 13, 1991, abandoned.

[51] Int. Cl.⁶ .............................................. A61L 2/16
[52] U.S. Cl. ............................. 422/30; 422/28; 422/312; 422/300; 134/901; 206/5.1; 514/840
[58] Field of Search ................. 422/28, 30, 292, 300, 422/310, 312; 514/839, 840; 210/679, 681, 683, 691, 692; 134/901; 206/5.1; 252/94, 106

[56] References Cited

U.S. PATENT DOCUMENTS

| | | | |
|---|---|---|---|
| 3,695,280 | 10/1972 | Sturgeon | 134/166 R |
| 4,029,817 | 6/1977 | Blanco et al. | 514/496 |
| 4,128,662 | 12/1978 | Lover et al. | 514/561 |
| 4,145,304 | 3/1979 | Melnick et al. | 210/502.1 |
| 4,174,277 | 11/1979 | Melnick et al. | 210/679 |
| 4,312,833 | 1/1982 | Clough et al. | 422/30 |
| 4,388,229 | 6/1983 | Fu | 252/549 |
| 4,661,344 | 7/1987 | Relenyi | 424/78.27 |
| 4,731,192 | 3/1988 | Kenjo et al. | 252/95 |
| 4,826,658 | 5/1989 | Kay | 422/30 |
| 4,852,591 | 8/1989 | Wisotzki et al. | 134/57 R |
| 4,863,627 | 9/1989 | Davies et al. | 252/95 |
| 4,889,693 | 12/1989 | Su et al. | 422/113 |
| 4,986,963 | 1/1991 | Corcoran et al. | 422/30 |
| 5,037,647 | 8/1991 | Chowhan et al. | 424/78.04 |
| 5,056,689 | 10/1991 | Heyl et al. | 222/189 |
| 5,059,402 | 10/1991 | Seamons et al. | 422/300 |
| 5,080,800 | 1/1992 | Heyl et al. | 210/679 |
| 5,129,410 | 7/1992 | Ifejika | 134/32 |
| 5,131,532 | 7/1992 | Ives | 422/300 X |

FOREIGN PATENT DOCUMENTS

| | | |
|---|---|---|
| 618389 | 2/1990 | Australia . |
| 622760 | 9/1990 | Australia . |
| 635285 | 1/1991 | Australia . |
| 0079030 | 5/1983 | European Pat. Off. . |
| 0196075 | 10/1986 | European Pat. Off. . |
| 0251211 | 1/1988 | European Pat. Off. . |
| 0359574 | 3/1990 | European Pat. Off. . |
| 175245 | 3/1977 | New Zealand . |
| 209331 | 6/1987 | New Zealand . |
| 209332 | 1/1988 | New Zealand . |
| 9002807 | 7/1992 | New Zealand . |
| 2214328 | 8/1989 | United Kingdom . |

Primary Examiner—Robert J. Warden
Assistant Examiner—Theresa T. Snider
Attorney, Agent, or Firm—Wenderoth, Lind & Ponack

[57] ABSTRACT

A method is provided for the sterilization or disinfection of an object in need of such treatment. The object is immersed in a sterilizing or disinfecting solution containing an antimicrobial effective amount of at least one cationic or at least one anionic antimicrobial agent in the presence of a scavenger element containing a scavenger material which is a cationic exchange resin or an anionic exchange resin. Over a period of time, the scavenger element removes from the solution the cationic or anionic antimicrobial agent at a rate which permits sterilization or disinfection of the object and which prevents undesirable build-up of the antimicrobial agent in or on the object. The object is allowed to remain in the solution for a time sufficient for the scavenger element to remove a sufficient amount of the antimicrobial agent to render the object safe for use for its intended purpose and the object is then removed from the solution. The method is particularly useful in the sterilization or disinfection of contact lenses. An apparatus for sterilizing or disinfecting objects in need of such treatment is also disclosed.

26 Claims, 5 Drawing Sheets

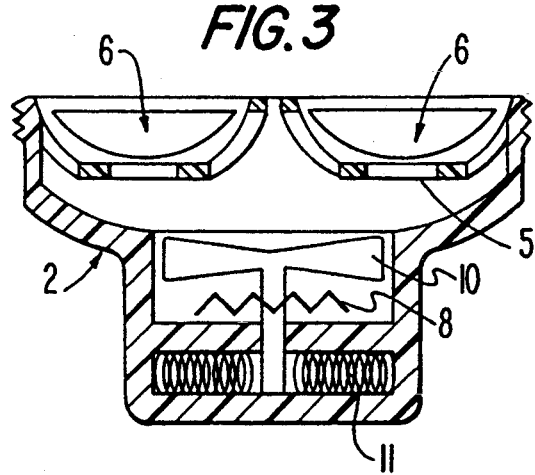
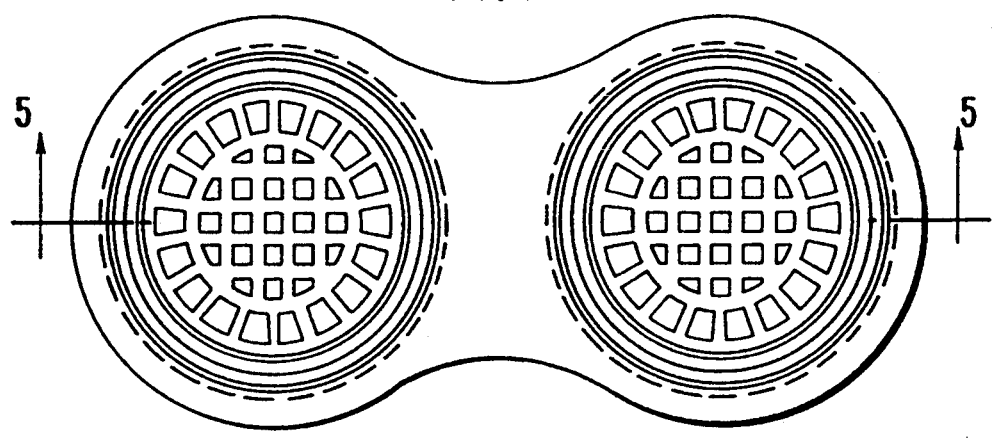
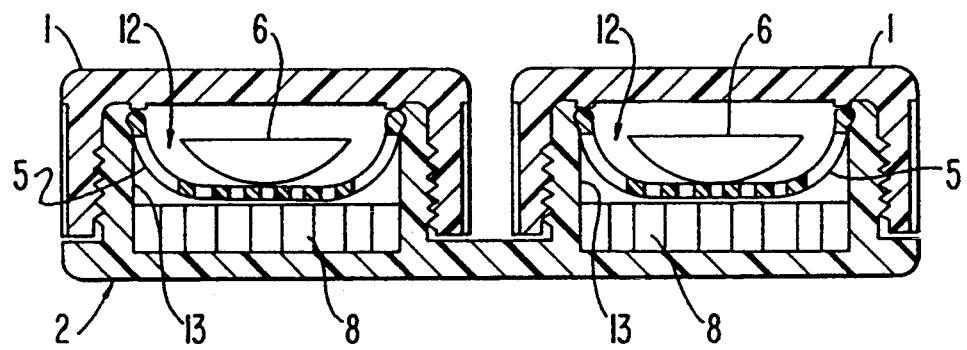

METHOD AND CONTAINER FOR STERILIZING AND DISINFECTING

This application is a continuation of now abandoned application Ser. No. 07/877/,706, filed May 4, 1992, which is a continuation-in-part of application Ser. No. 857,481, filed Mar. 25, 1992, (now abandoned) which is a continuation-in-part of application Ser. No. 07/791,248, filed Nov. 13, 1991(now abandoned).

This invention provides a method and container for sterilizing or disinfecting. While the invention is principally directed to a method and container for sterilizing or disinfecting contact lenses, it is also applicable to various other fields as will be apparent from the description set forth below.

BACKGROUND OF THE INVENTION

In recent years, there has been a tremendous increase in the use of contact lenses. This has, in part, coincided with the expansion of polymer and plastics technology. Various types of contact lenses have become available including hard, rigid, gas-permeable, flexible and soft hydrogel depending upon the characteristics of the materials employed to form the lens. The soft hydrogel lenses are normally formed from cross-linked hydrophilic polymers and copolymers such as 2-hydroxyethylmethacrylate, 2,3-dihydroxypropylmethacrylate, methylmethacrylate, methacrylic acid, N-vinyl-2-pyrrolidone, etc., which can be hydrated with 20–85 percent water. See Refojo, *Encyclopedia of Chemical Technology*, Kirk-Othmer, Vol. 6, 3rd Edition (1979), pages 720-2.

Various problems are encountered in the sterilizing or disinfecting of contact lenses. It is, of course, mandatory that sterilization or disinfection of the lenses be achieved prior to introduction of the lens into the eye. The eye is an extremely sensitive organ and certain types of microbial infection can cause damage or even blindness in a very short time. Also, in view of the sensitive nature of the eye, especially in certain individuals, it is important to avoid as much as possible contacting the eye with the agents which are effective in destroying microorganisms responsible for causing microbial infection.

Many antimicrobial agents are known which are useful to achieve sterilization or disinfection of contact lenses. Among these are chlorhexidine, thimerosal, benzalkonium chloride, Bradosol ® and the like. These agents are known to provide especially good sterilizing and disinfecting properties. It is known, however, that over time these agents can become concentrated in the hydrogel soft contact lenses and may be subsequently released onto the cornea of the eye during wearing of the lenses. This can cause chemical burning of the cornea and/or an allergic response in the wearer even at low concentrations.

Fu, in U.S. Pat. No. 4,388,229, has proposed a contact lens rejuvenating solution which is said to be useful in removing occluded and adsorbed cationic and anionic agents such as bactericides, preservatives and germicides from contact lenses. In accordance with Fu, a contact lens which has a build-up of the cationic or anionic agent is subjected to treatment with the solution to remove the agent and thereby rejuvenate the lens.

Fu does not provide a sterilizing or disinfecting solution for the lens. Fu provides a solution which is useful in conjunction with and as a separate step from a sterilizing or disinfecting system. The lenses are separately subjected to sterilizing or disinfecting and then, after build-up of the chemical agent in the lenses has occurred, they are subjected to rejuvenation with the Fu solution.

A further problem with the Fu solution would appear to be one of storage stability. The formulation of Fu would have to be maintained under sterile conditions since it could not itself contain any cationic or anionic preservative agent since such agent would be taken up by the cationic and/or anionic exchange resin in the formulation. Thus, a long time storage of the Fu formulation by the user after opening would appear to be precluded.

Heyl et al., U.S. application Ser. No. 461,988, filed Jan. 8, 1990 (now U.S. Pat. No. 5,056,689), discloses methods and devices for removing preservatives from ophthalmic solutions. In accordance with Heyl et al., a dispensing device is provided which contains an ophthalmic solution containing a preservative agent such as a quaternary ammonium compound. The solution is dispensed from the container outlet which contains scavenging means for removing the preservative from the solution as it is dispensed through the outlet. Thus the solution exiting the container outlet is preservative-free. In accordance with that invention, the ophthalmic solution contacting the eye or a contact lens will not contain preservatives.

THE PRESENT INVENTION

The object of the present invention is to provide a one-step system for the sterilization or disinfection of—in particular—contact lenses which system employs the cationic or anionic disinfecting and sterilizing agents in order to achieve their especially good antimicrobial properties and yet avoids the known problem of build-up of these agents in the soft hydrogel lens over time.

The invention also provides a container to be employed in this sterilization or disinfecting system.

The system and container of the invention are also useful for the sterilization or disinfection of other objects such as, for example, medical objects, i.e., surgical and dental implements and the like.

The invention provides a method for the sterilization or disinfection of an object requiring such treatment—such as a contact lens—comprising immersing said object in a sterilizing or disinfecting solution in a container, said solution comprising at least one cationic antimicrobial agent or anionic antimicrobial agent wherein said container also contains a scavenging material which, over a desired period of time, will sufficiently remove from the said solution the cationic antimicrobial agent or anionic antimicrobial agent and which will prevent any undesirable build-up of the said antimicrobial agent in or on the object to be sterilized or disinfected.

It is not essential that the scavenging material remove all of the antimicrobial agent from the solution. It is only necessary that the level of the antimicrobial agent be reduced to a level where it is safe to employ the sterilized or disinfected article for its intended use. For example, in the case of a contact lens such lens can be introduced into the eye of a wearer safely even where the content of, for example, chlorhexidine in the solution is up to about 20 parts per million of the solution. In point of fact in some cases it is desirable that the scavenger material does not scavenge from the sterilizing or disinfecting solution all of the antimicrobial agent present. In such case, a sufficient amount of such agent will remain in the solution to retain a preservative effect and thus permit a rather long time storage of the sterilized or disinfected article in the solution in the container after sterilization or disinfection has been achieved.

In the case of an object such as a soft hydrogel contact lens where build-up of the antimicrobial agent in the object itself occurs, it is not essential that all such build-up be prevented. Thus, herein the term "undesirable" is used in conjunction with the term "build-up". As used herein "undesirable" is intended to mean a level of antimicrobial agent content which renders the object to be sterilized or disinfected unsuitable for use for its intended purpose. An antimicrobial agent content below that level in or on the object is permitted.

It is contemplated that the sterilizing or disinfecting solution will be provided in bulk form to be employed by the user in portions as needed. Such solution can be added in the proper amount to the container in which sterilization or disinfection will be carried out and the object or objects to be treated can be immersed in such solution. The container to be employed will be described in more detail subsequently herein.

The sterilization or disinfecting solutions to be employed can be those which are known in the art which employ cationically charged or anionically charged antimicrobial agents. The antimicrobial agents can be employed singly or as mixtures of the materials.

Positively charged antimicrobial agents which can be employed include, but are not limited to, chlorhexidine and its derivatives such as the diacetate and digluconate and quaternary ammonium compounds such as Bradosol ®, benzalkonium chloride (BAK), cetyl ammonium chloride and others. The sterilizing and disinfection properties of these materials are well known as is their specific use in the treatment of contact lenses.

Negatively charged antimicrobial agents which can be employed include, but likewise are not limited to, sorbic acid. Such materials are also known as sterilizing and disinfecting agents and their specific use in treating contact lenses is also known.

The content of the antimicrobial agent or agents in the solution will be that amount necessary to achieve sterilization or disinfection of the object immersed in the solution. This will vary somewhat with the object to be treated and with the particular antimicrobial agent(s) employed. In the case, for example, of the treatment of contact lenses with a solution containing chlorhexidine, the amount of chlorhexidine can be from about 50 to about 100 parts by weight of chlorhexidine per million parts by weight of the solution.

The container into which the solution is placed will contain a scavenger element (to be described in more detail later herein) which will, over time, extract the antimicrobial agent(s) from the sterilizing or disinfecting solution. The level of content of antimicrobial agent in the starting solution added to the container and the rate of extraction of the agent by the scavenger material are chosen such that the antimicrobial agent content of the solution will remain sufficiently high for a sufficient time period that satisfactory sterilization or disinfection of the object is achieved. For example, when employing chlorhexidine as the antimicrobial agent in an amount of about 50 ppm, it has been found that when treating contact lenses if a scavenger element is employed which scavenges the chlorhexidine at a rate such that after a 30 minute contact time with the solution, the solution contains about 30 ppm chlorhexidine such system is sufficient to achieve sterilization or disinfection of the lens.

Once the necessary sterilization or disinfection of the object has been achieved, the scavenger material may continue to extract the antimicrobial agent down to zero content or to a level which will enable the safe employment of the object for its intended use.

In one embodiment of the invention it is desired that the level of the content of the antimicrobial agent be reduced only down to a level at which it will exert preservative effect on the solution thereby preventing microbial growth over a reasonably long period of time. This embodiment can be illustrated in connection with the treatment of contact lenses. A contact lens case containing mesh holders for the lenses and a scavenger element can be filled with a solution containing about 50 ppm chlorhexidine. The lenses can be placed in the case and the case sealed. The scavenger element can be selected such that over a period of about 60 minutes there is a fairly constant rate of extraction of the antimicrobial agent from the solution by the scavenger element such that the content of the chlorhexidine is reduced to a level of about 10 ppm. This rate of extraction will permit sterilization and disinfection of the lenses to be obtained. At this point in time, the level of chlorhexidine in the solution is sufficiently low that the lenses may be safely removed from the solution and placed in the eye of the wearer although sterilization may not be complete. The lenses are preferably left in the solution until sterilization is complete. From about 60 minutes to about 400 minutes the scavenger element will continue to extract the chlorhexidine from the solution at, however, a more gradual rate until, at about 400 minutes, the level of chlorhexidine is about 7 to 8 ppm. This permits completion of the sterilization and this level of chlorhexidine content is sufficient to provide a preservative effect on the solution to prevent microbial growth and will permit the lenses to remain in the solution in a sterilized condition for a rather long storage period, for example, overnight or longer, i.e., up to about 30 days.

Additionally, in the case of objects where build-up of the antimicrobial agent on or in the object may occur, such as soft hydrogel contact lenses, the scavenger element is selected to prevent such build-up to an undesirable level. As an example, it is known that chlorhexidine build-up occurs in soft hydrogen contact lenses. In a 30 day cycling program using a chlorhexidine sterilizing solution without a scavenger element, it has been found that after 30 cycles (one sterilization cycle per day) the amount of chlorhexidine in the soft hydrogel lens can reach a level where there will be a cytotoxic response. By cytotoxic response is meant a response that would cause a reaction of some kind in the eye of a lens wearer. This is sometimes referred to as "red eye" syndrome. It is for this reason that chlorhexidine has not been used more as a sterilizing or disinfecting agent for soft hydrogel contact lenses. By employing the present invention it is possible to avoid the build-up of chlorhexidine in the lens to a level where the cytotoxic response occurs.

Additional materials can be employed in the sterilizing or disinfecting solution. Such solution is basically a sterile aqueous solution containing the necessary antimicrobial agent component as indicated previously. The additional materials must be ones which are compatible with—or do not interfere with—the interaction of the scavenger element and the antimicrobial agent. These additional materials should also be of the type and be used in amounts which will be safe when employing the sterilized or disinfected article for its intended use at the end of the treatment. For example, it is contemplated that when treating contact lenses, at the completion of the sterilization or disinfection treatment—or after overnight storage in the container in which the treatment has been conducted—it will be possible for the lens wearer to simply remove the lenses from the container and place them in the eye without further treatment. Thus, any additional materials present in the treatment solution should be materials which are of the type and should be employed in amounts which will permit the introduction of the lenses into the eye directly from the case without further treatment.

Examples of additional materials which can be employed are as follows:

Buffers

Buffer materials can be employed such as borates or phosphates to provide the desired pH of the solution.

EDTA

EDTA or salts thereof can be employed for chelating metals and possible enhancement of antimicrobial activity.

Surfactants

Various surfactants can be employed as possible conditioning agents for contact lenses and for possible enhancing of the antimicrobial activity as well. Triton X-100 may be mentioned as an example.

Wetting Agents

Optionally wetting agents can be included such as polyvinyl alcohol, polyvinyl pyrrolidone, hydroxypropyl methyl cellulose and hydroxyethyl cellulose.

NaCl

Sodium chloride can be employed to provide the desired isotonicity for the solution.

Scavenger Element

For the scavenger element of the present invention use is made of the basic principal that positive and negative charges attract. This basic principal has been taken advantage of in the previously discussed prior commonly owned application Ser. No. 461,988 filed Jan. 8, 1990 (now U.S. Pat. No. 5,056,689) as well as in the previously discussed Fu U.S. Pat. No. 4,388,229. However, neither the prior application nor the prior patent teaches or suggests the employment of a scavenger element in a sterilization or disinfection system as provided by the present invention.

The specific material employed in the scavenger element is selected to complement the antimicrobial agent(s) employed in the sterilization or disinfecting solution. Thus, if a negatively charged antimicrobial agent or mixture thereof is employed in the solution, a positively charged material will be employed in the scavenger element and vice versa.

In general, the positively or negatively charged material employed in the scavenger element will be an ion exchange material of the cationic or anionic type. Various types of suitable materials are discussed in detail in prior application Ser. No. 461,988 (now U.S. Pat. No. 5,056,689) and U.S. Pat. No. 4,388,229 the disclosures of which are incorporated herein by reference. The scavenger element itself can take a number of different forms. In one embodiment the container into which the sterilizing or disinfecting solution is added is itself made of or is coated with a material which scavenges the antimicrobial agent from the solution. Examples of such materials are polymer materials which have been subjected to sulfonation or carboxylation reactions. In another embodiment, the scavenging material such as a cationic or anionic exchange resin is packaged in a permeable container such as in a "teabag" form which is then placed in the container. In a still further embodiment, the ion exchange resin is incorporated into a paper such as a filter paper to form a scavenger element which is then placed in the container to which the solution will be added. Also, the element can take the form of a membrane in which the exchange resin is incorporated such as Sybron chemical cationic exchange membrane IONAC MC 3142.

In a still further embodiment the desired exchange resin can be blended with a prepolymer which is then subjected to polymerization. The resultant polymer material can then be subjected to a forming operation resulting in the formation of the scavenger element in the desired form such as a disc.

As a still further alternative, the cationic or anionic exchange material can be incorporated into an already formed polymer such as a polyurethane or polyethylene resin. The mixture can be melt blended or crosslinking can be carried out as necessary and the resultant mass can then be subjected to a forming operation resulting in the formation of the scavenger element in the desired form. The following materials have been used as inserts to a contact lens case. These are in filter paper form.

Bio-Rad Laboratories Products

Ag-50
Chelex

Whatman

P-81
CM30
CM50

Gelman Sciences

ICE-450

In addition, various resins have been employed by placing them in a "teabag" type container.

Sybron Chemical

C249
C269

Whatman

CM92
SE92
SE52

Bio-Rad Laboratories Ag-50 Chelex BioBeads Sm-7

Rohm & Haas

Amberlite

Illustrative of a membrane type scavenger element is Sybron Chemical cationic exchange membrane IONAC MC 3142.

In one embodiment of the invention, the scavenging material which may be employed is an N-acyl sarcosine, i.e., N-acyl-N-methyl glycine. These materials are well known as surface active agents and also have ovicidal and insecticidal properties. See U.S. Pat. No. 4,128,662.

The materials are marketed as Hamposyl ® surfactants by W. R. Grace & Co. These materials are useful particularly as the scavenging material when employing a quaternary ammonium compound such as Bradosol ® as the antimicrobial agent in the sterilizing or disinfectant solution.

These particular scavenging materials have the ability to not only scavenge the antimicrobial agent from the solution but also to prevent the up-take of the antimicrobial agent by the soft hydrogel contact lens. It is believed that this may involve a coating of the lens by the agent as a result of its surfactant properties.

The N-acyl sarcosines are particularly valuable in respect to the sterilization or disinfecting of contact lenses in view of their very low ocular irritation properties.

The particular method of employing these materials is described in more detail later herein.

The Method

In carrying out the method of the invention, a container containing the scavenger element or to which the element is to be added is provided. To the container can then be added the required amount of the sterilizing or disinfecting solution. The amount will be sufficient for the object which is to be sterilized or disinfected to be immersed in the solution. Alternatively, of course, the object to be treated may first be placed in the container and the solution subsequently added in the requisite amount. The container is then preferably sealed to the extent necessary to exclude the possibility of microbes being introduced from the surrounding environment. The object is permitted to remain in the container for a sufficient time to ensure that sterilization or disinfection is complete and to ensure that the required amount of the antimicrobial agent has been scavenged from the solution to render it safe to employ the sterilized or disinfected object for its intended purpose. At this point in time, the container may be opened and the object removed and employed in its normal use. Prior to such use a rinsing step can be employed if desired. In the case of contact lenses of the soft hydrogel type, it is contemplated that the minimum storage time in the solution will be about 30 minutes to about 1 hour. At the end of this time period a sufficient amount of the antimicrobial agent has been scavenged and the container may be opened and the lens removed and placed in the eye safely without further treatment. At this point in time, however, sterilization may not be complete, and it is preferred that the lens be retained in the solution until sterilization or disinfection is complete. Alternatively, the lenses may be left in the sealed container in the solution for a longer period of time as, for example, overnight or even up to 30 days. They will remain in a sterile condition during such storage.

In some cases it is desirable that the object to be sterilized or disinfected according to the invention be subjected to a pretreatment, such as a cleaning and/or conditioning pretreatment prior to the treatment in accordance with the invention. In the case, for example, of soft hydrogel contact lenses, such lenses may be removed from the eye of the wearer and initially subjected to treatment with cleaning and conditioning solutions which are well known in the art. Following such pretreatment the lenses can be subjected to the sterilizing or disinfecting treatment of the present invention.

In a particularly preferred embodiment, the antimicrobial solution used herein is used as a single care solution for the cleaning and sterilization or disinfecting of the soft hydrogel contact lenses. In such embodiment the lenses are removed from the eye of the wearer and the antimicrobial solution is applied to the lenses with a mild rubbing between the thumb and forefinger. The lenses are then rinsed with the solution and placed in the container in which the sterilization or disinfection will be carried out. A sufficient amount of the solution is then added to the container to immerse the lenses and the container is closed. After the requisite amount of time, the lenses can be removed from the container and reintroduced into the eye of the wearer.

The Container

In a further aspect of the invention there is provided an apparatus which is a container for carrying out the method of the invention. In its broadest form the container is one which contains a scavenger element, is of a size and shape adapted to receive the object or objects to be sterilized or disinfected and will contain a sufficient amount of a sterilizing or disinfecting antimicrobial solution in which to immerse the said object or objects therein. The container also has sealing means to render the container substantially air-tight.

In this general context the shape and size of the container is not critical. The important factor in this regard is that it be of a shape and size which will permit the introduction thereinto of the object or objects to be treated by the inventive method and of a sufficient amount of the antimicrobial agent—containing solution for immersion of the said object or objects therein.

The container also contains the scavenger element. As previously discussed, the scavenger element can be a separate element which is placed in or secured to the container or it can be an integral part of the container such as the instance where the container itself is formed from or coated with a material which scavenges the antimicrobial agent from the solution. An example of the latter is a sulfonated styrene resin.

It is apparent that the container is to be constructed such that the solution containing the antimicrobial agent will be in contact with the scavenger element or material and circulation of the solution in, around and/or through the scavenger element or material is permitted so that the element or material performs its function of scavenging the antimicrobial agent from the solution to the necessary extent.

While not obligatory, it is desirable that the container have means for sealing it in order to isolate the object to be treated from the surrounding environment. This has the function of preventing the introduction into the solution of any additional microbes such as airborne microorganisms. It also serves to prevent spillage of the solution from the container during handling. Absolute sealing of the container to make it pressure tight, while not essential, may, in certain instances, be preferable. It is also possible to provide the container with sealing means which include a filtration means for filtering airborne microbes from any air entering the container after sealing. Such filtering means are known in the art.

In general, however, it is sufficient that the sealing means will constitute a container top either separate from or formed as an integral part of the container which can be opened by the user to permit access to the interior of the container and closed after introduction of the object or objects to be treated and the sterilizing or disinfecting solution along with the scavenger element or material if such element is not provided in a fixed condition to the container.

This container aspect of the invention will be described in more detail below with reference to a contact lens case which is a presently preferred embodiment of the invention. Reference in this regard will be made to the attached figures of drawings.

BRIEF DESCRIPTION OF DRAWINGS

The figures of drawings may be briefly described as follows:

FIG. 3 is a cross-sectional view of a further container of the invention.

FIG. 4 is a plan view of a container of the invention.

FIG. 5 is a cross-sectional view taken along line 5—5 of FIG. 4.

DETAILED DESCRIPTION

Figure 1:
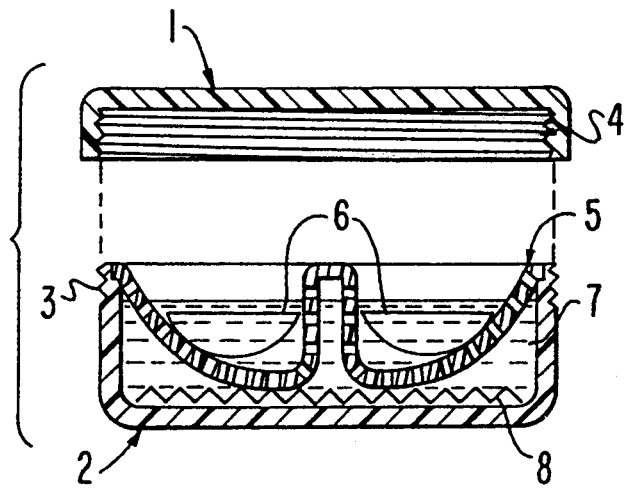
FIG. 1 is a cross-sectional view of an essentially cylindrical container of the invention.

Referring to FIG. 1, a container for contact lenses is shown which is composed of a top closure 1 and the main body 2 of the container. The container is cylindrical in shape and the sidewalls contain screw threads 3 which mate with the screw threads 4 on the top closure portion of the unit.

The unit contains a mesh contact lens holder 5 which defines separate areas for holding two contact lenses 6. The container is sufficiently large to permit the introduction of a sufficient amount of antimicrobial solution 7 so that the contact lenses, when placed in the lens holder areas will be immersed in (completely covered by) the solution. Below the mesh lens holder there is provided a scavenger element 8. This element can take the form of a substrate, such as paper, which is coated or impregnated with a cationic or anionic exchange resin or a membrane containing the exchange resin. Examples of the element are materials such as Sybron Chemical cationic exchange membrane IONAC MC 3142, Bio-Rad Laboratories AG-50 paper or Whatman cellulose paper incorporating SE92 or CM 92. These materials are, of course, purely illustrative and others can be employed. In FIG. 1, the scavenger element is shown in the form of a disc which is concentrically accordionally pleated.

The container can be formed from a plastic material such as has previously been employed in forming contact lens cases. Examples of these materials are food grade polyethylene and polypropylene. Such materials are well known in the art.

The lens holder 5 is formed so as to permit the antimicrobial solution to freely circulate around the contact lenses and the scavenger element. In the embodiment of FIG. 1 the lens holder is a mesh material which can be formed from the same or a similar plastic material used to form the body of the container, i.e., food grade polypropylene.

The scavenger element and the container can be designed for the element to be removable from the container as, for example, in the instance where the scavenger element is used for only one sterilization or disinfecting cycle and a new element is employed for the next cycle. In a more practical embodiment, however, the element and the container are designed such that the scavenger element will not be removed from the container by the user. In such case the scavenger element is designed for multiple cycle use such as, for example, a period of about one month during which time it performs the scavenging function on a daily basis.

FIGS. 6 to 11 show a plurality of exemplary forms which the scavenger element can take. For example, 6a is a plan view of a scavenger element in disc form with FIG. 6b being a cross-sectional view of FIG. 6a taken along line 6b—6b. This element can be, for example, formed from a filter paper impregnated with ion exchange resin or, as another alternative, it may be formed from a membrane material such as Sybron Chemical cationic exchange membrane IONAC MC 3142.

Figure 11A:
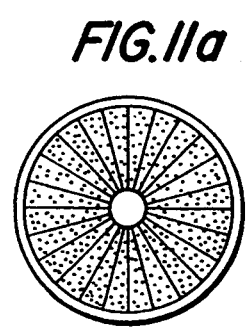
FIGS. 11a and 11b are respectively a plan view and a cross-sectional side elevational view of a scavenger element of the invention.
Figure 9B:
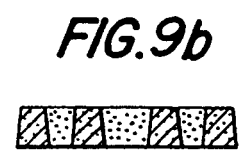
Figure 10B:
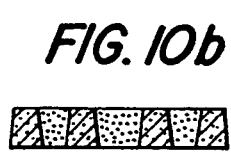
Figure 11B:
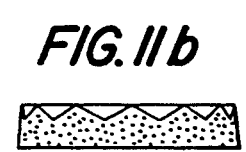

In another particular embodiment, FIG. 11a is a plan view of a scavenger element which is essentially in disc form which is concentrically accordionally pleated. FIG. 11b is a cross-sectional side elevational view of FIG. 11a. The pleating arrangement allows for circulation of the antimicrobial solution around the full surface of the element.

Figure 8A:
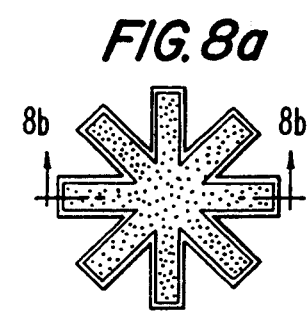
Figure 6B:
Figure 7B:
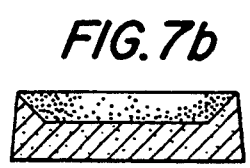
Figure 8B:
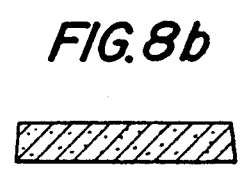
Figure 9A:
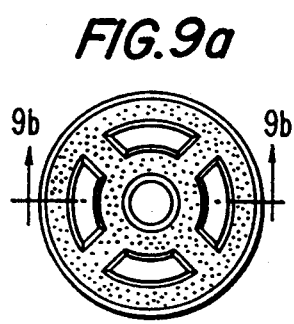
Figure 10A:
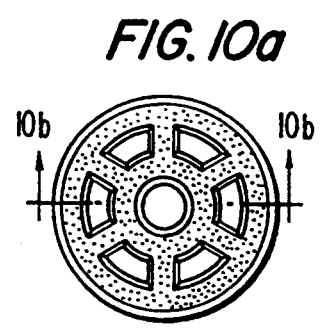

An especially useful embodiment is shown in FIG. 8a and FIG. 8b. FIG. 8a is a plan view of the embodiment and FIG. 8b is a cross-sectional view taken along line 8b—8b of FIG. 8a. This embodiment can be referred to as a "flower" form in which "petals" radiate out from the center, or as a disc having cutaway portions to form essentially equispaced radial arms.

The scavenger element can, of course, take other forms as for example a "teabag" form in which an exchange resin is sealed in a porous material to allow circulation of the antimicrobial solution for contact with the exchange resin.

The above are merely illustrative and not exhaustive of the forms which the scavenger element may take.

Figure 2:
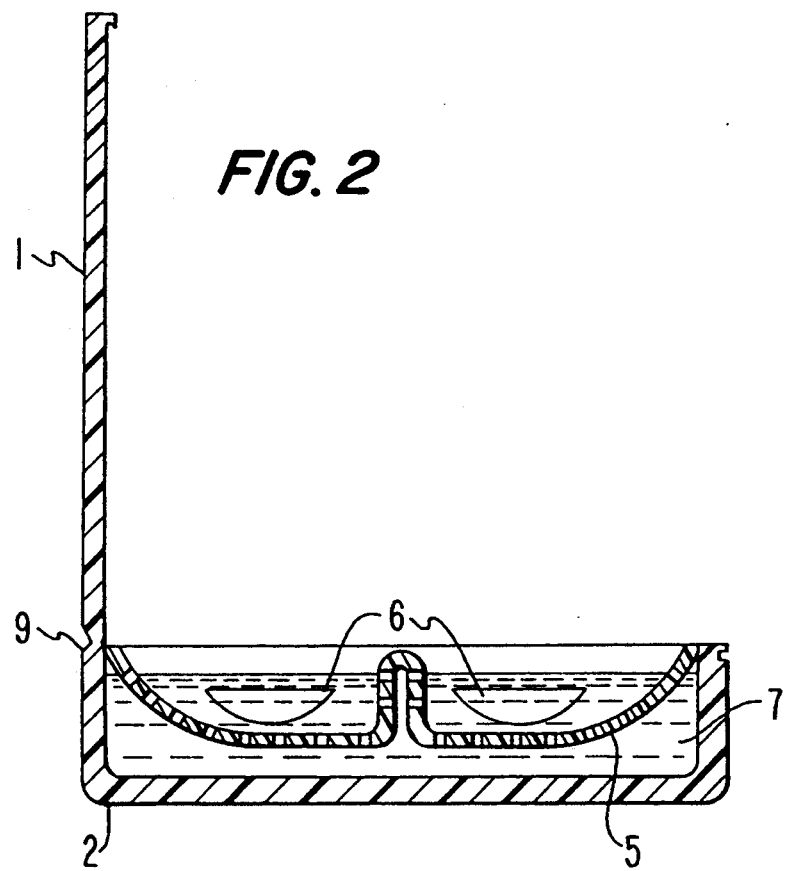
FIG. 2 is a cross-sectional view of an essentially cylindrical container of the invention.
Figure 6A:
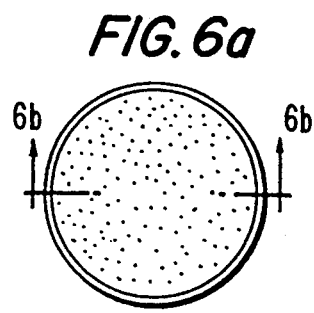
FIGS. 6a and 6b, 7a and 7b, 8a and 8b, 9a and 9b, 10a and 10b are respectively plan views and corresponding sectional views of various scavenger elements of the inventions.
Figure 7A:
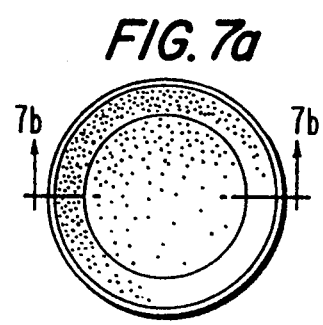

FIG. 2 shows a further embodiment of the invention in which the container itself and/or the holder for the contact lens itself acts as the scavenger element. FIG. 2 is a cross-sectional view of the essentially cylindrical container.

In FIG. 2, the main body 2 of the container, which is cylindrical in shape forms a reservoir for the antimicrobial solution 7 to be added by the user. A mesh lens holder 5 defines separate areas for holding two contact lenses 6. The top closure portion 1 is pivotably connected to the main body 2 by a flexible hinge 9. The main body 2 and the top closure portion 1 are constructed such that the top closure portion can be snap fit to seal the container.

In this embodiment the main body 2 and/or the mesh lens holder 5 are formed from or are coated with a scavenging material and thus either or both elements constitute the scavenger element.

In a further embodiment a container such as that of FIG. 2 can be provided in which neither the main body 2 nor the mesh lens holder 5 constitutes the scavenger element. In such instance the scavenger material, for example, in the form of a liquid or a solid material can be added to the container in a predetermined amount satisfactory for a single sterilization or disinfecting cycle treatment. This embodiment would be effective, for example, when using a material such as an N-acyl sarcosine (Hamposyl ®) as the scavenging material as discussed above herein.

In a further embodiment the container can be constructed to provide means for forcing circulation of the antimicrobial solution around the contact lens and the scavenger element. This embodiment is shown in FIG. 3 which is a cross-sectional view of the container.

In this embodiment, the main body 2 of the container is shown without the top closure portion which can, of course, be provided in a desired form. Means for holding contact lenses 6 is provided by the lens holder 5. A scavenger element 8 is provided below an impeller blade 10 which is driven by a motor 11. The motor can be driven by electrical means as desired and not shown.

The lens holder is designed to permit antimicrobial solution added to the container to circulate therethrough for contacting the contact lenses. Circulation of the antimicrobial solution is forcibly created by the impeller blade 10 and such solution is also caused to contact the scavenger element. In this manner, improved circulation of the antimicrobial solution for contact with both the contact lenses and the scavenger element is achieved.

A still further embodiment of the container is shown in FIG. 4 and FIG. 5. FIG. 4 is a plan view and FIG. 5 is a cross-sectional view taken along line 5—5 of FIG. 4. In this embodiment, separate chambers 12 are provided for the two contact lenses 6. The chambers are defined by the cylindrical walls 13 of the main body 2 of the container. Each of the chambers is provided with a mesh lens holder 5. Each of the chambers is also provided with a scavenger element 8.

The container is shown with each of the chambers fitted with a removable top closure portion 1 which closure portions contain screw threads which mate with the screw threads on the outer portion of the walls 13 of the main body 2 of the container. This allows sealing of each of the separate chambers following introduction of the contact lens and the desired amount of the antimicrobial solution.

A further embodiment of the present invention includes means for agitating the container holding the antimicrobial solution, scavenger elements and lenses. The purpose of the agitating means is to reduce the amount of time required to remove disinfecting and preserving agents from the solution by causing the solution to repeatedly wash over the scavenger elements. The agitation may be caused by a number of different motions, including, but not limited to, shaking and swirling. The degree of removal will be influenced by the rate of agitation, the volume of solution and the concentration of the antimicrobial agent.

Figure 13:
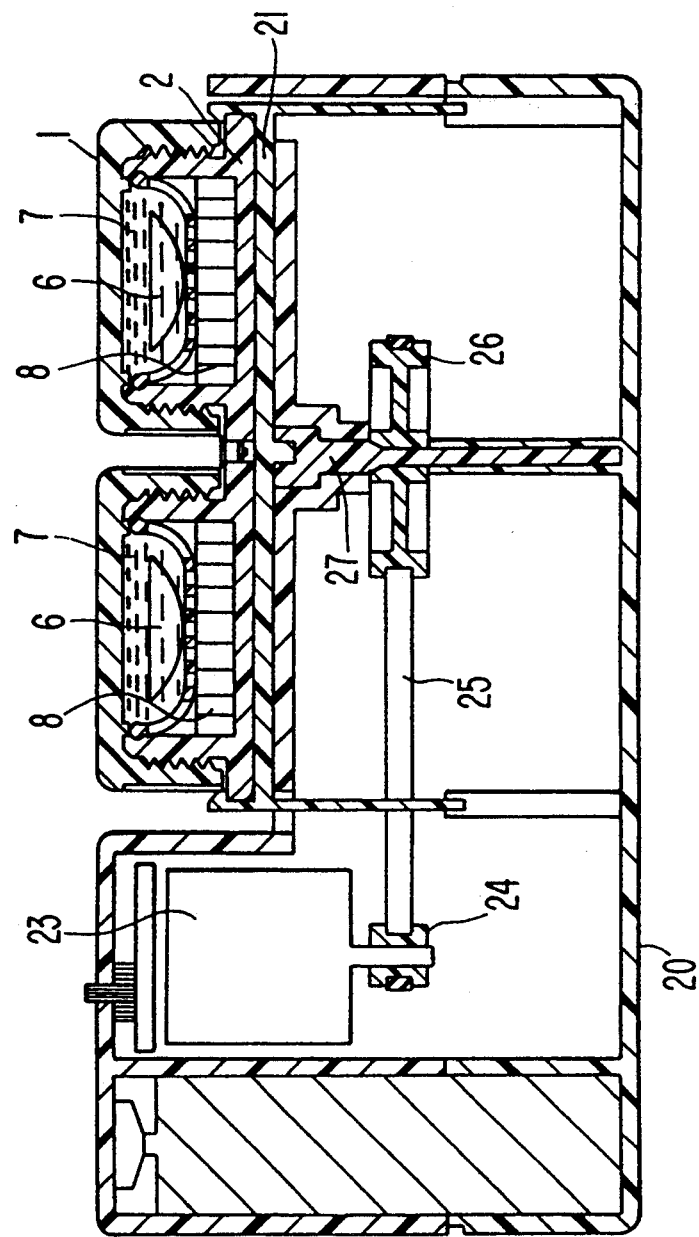
FIG. 13 is a cross-sectional view of an embodiment of the invention in which the container of the invention is subjected to agitation.

FIG. 13 is a cross-sectional view of an example of means for agitating the container according to the present invention. A container, including top closure 1, main body 2 and scavenging elements 8, holds two contact lenses 6 and a sufficient amount of antimicrobial solution 7 to immerse the lenses. The means for agitating the container is preferably an electrically operated device 20, and includes a container support 21 and an electric motor 23 for rotating or otherwise moving the container support 21. In operation, the container holding the antimicrobial solution, scavenger elements and lenses is placed onto the container support 21. After a predetermined time set to coincide with the end of the initial disinfection period, the motor 23 is started, rotating drive pulley 24 and translating energy through drive bolt 25 to activation pulley 26. The rotating activation pulley 26 rotates a decentric drive shaft 27, which is attached to the container support 21. The rotation of the drive shaft 27 moves the container support 21 about the center of rotation of the activation pulley 26 in a radius determined by the decentration of the drive shaft 27. The device 20 agitates the container in a small circle, allowing continuous motion and forces the solution to be mixed and to make repeated contact with the scavenger elements 8.

EXAMPLE

The following example is provided in order to illustrate the invention. The example is purely illustrative of the invention.

A contact lens container similar to that illustrated in FIG. 4 and FIG. 5 is employed. The container is one molded from food grade polypropylene. The mesh lens holder is also formed from food grade polypropylene.

The scavenger element employed in each of the chambers is a disc of cationic exchange membrane IONAC MC 3142 similar to that of FIG. 8a and 8b. Into each of the separate chambers is placed an inoculated contact lens (inoculation as described below) and each of the chambers is filled with a sterile aqueous antimicrobial formulation containing the following components:

0.1 m borate buffer
0.1% EDTA
50 ppm chlorhexidine (Cx24
25 ppm Triton X-100
0.2% PVP
0.3% NaCl The pH of the formulation is about 7.

Inoculation of the contact lenses is carried out in the following described manner.

The lenses employed are Softcon type IV EW lenses (Ciba Vision Corporation). Test microorganisms as are follows:

*Pseudomonas aeruginosa* ATCC 15442
*Serratia marcescens* ATCC 14041
*Staphylococcus epidermidis* ATCC 17917
*Candida albicans* ATCC 10231 and
*Aspergillus fumiqatus* ATCC 10894.

The organisms are cultured and harvested according to established procedures.

A challenge inoculum is prepared by suspending approximately $10^8$ CFU of each of the challenge organisms in one ml of organic soil which consists of heat-killed cells of *Saccharomyces cerevisiae* ($10^8$/ml) in heat-inactivated calf serum (Sigma).

Each of the lenses is inoculated with 20 μl (10 μl/side) of the challenge inoculum. Inoculated lenses are allowed to dry for 5 minutes before application of the antimicrobial solution described above. An inoculated lens is placed into the palm of a gloved hand. Three drops of the antimicrobial solution are applied to each lens surface and the lens is rubbed for 20 seconds with the index finger of the opposite hand. The lens is then rinsed with a steady stream of the antimicrobial solution for 10 seconds. The inoculated lens is then placed in the mesh lens holder of the container. Each of the chambers of the container is then filled with the antimicrobial solution.

Figure 12:
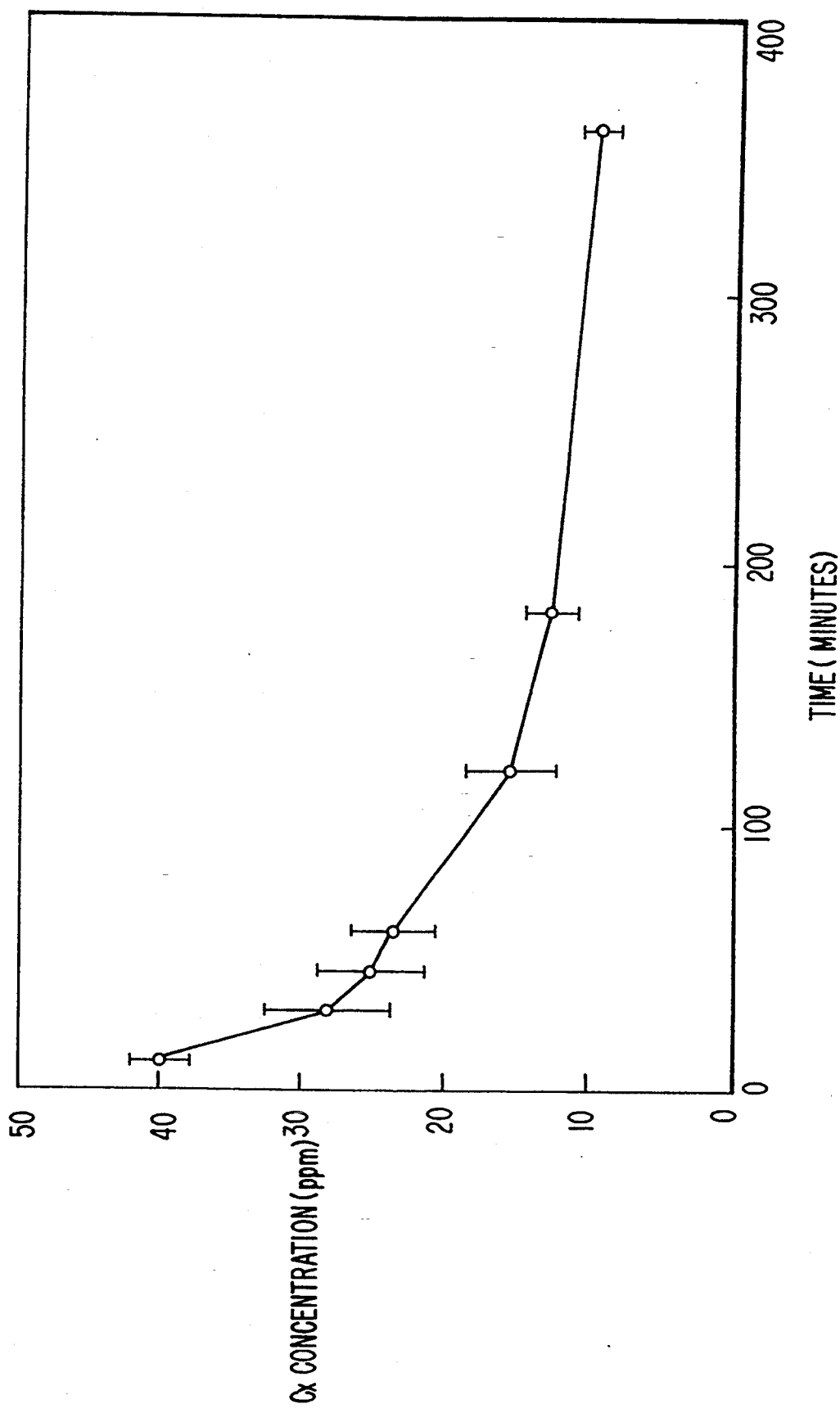
FIG. 12 is a graph showing reduction of chlorhexidine content in an antimicrobial solution over time.

At time intervals over about 360 minutes, the solution in each of the chambers of the container is evaluated for chlorhexidine (Cx) content. FIG. 12 is a graph which illustrates the reduction in Cx content in the solution over time.

After 6 hours the lenses are removed from the container with a sterile forceps and rinsed with a steady stream of antimicrobial solution for 10 seconds. Each of the lenses and the antimicrobial solutions in which the lenses had been immersed for 6 hours is cultured separately in Letheen Broth (Difco). Broths are incubated at 35° C. for fourteen days on a roller drum at 16 rpm.

The results establish that no viable bacteria or fungi remain on the treated lenses or in the treatment solutions thus confirming that sterilization and disinfection of the lenses has been achieved.

In a further embodiment, the scavenger element may take the form of a cellulosic material which has been dyed with a reactive dye containing at least one sufonic acid group. The cellulosic material may be one such as cotton, paper, cotton cloth or cellulosic sponge. The negatively charged sulfonic acid groups of the reactive dye act as a "scavenger" to attract quaternary ammonium salts, polyquaternary ammonium salts and other positively charged preservative or disinfecting agents.

The following example is illustrative of this embodiment of the invention.

Fifteen cellulosic sponge discs each having a diameter of ¾ inches and a height of ¼ inch were charged into a 2-liter beaker preheated to 60° C. 300 ml of 2% Cibacron Orange FR solution (available from Ciba-Geigy Corporation, Ardsley, N.Y.) was added to the beaker, followed by 100 ml of a mixture of 16% was added to the beaker, followed by 100 ml of a mixture of 16% Na$_3$PO$_4$.12 H$_2$O and 15% tetrabutyl ammonium bromide (2 to 1 volume mixture). After heating at 60° C. with stirring for about seventy-five minutes, an additional 150 ml of 2% Cibacron Orange FR solution and 50 ml of the Na$_3$PO$_4$.12 H$_2$O/tetrabutyl ammonium bromide mixture were added, followed by stirring for another seventy-five minutes. The sponges were then removed and rinsed with warm water for several minutes. The sponges were then placed in a 2 liter flask and boiled in deionized water for one hour, and the water was decanted. The washes were repeated until no color was present in the wash. The sponge was then pressed dry. The process was repeated using fresh sponges and a number of different reactive dyes, as set forth in Table 1 below. Two of the sponges were placed in 200 ml of an aqueous 50 ppm chlorhexidine solution. The sponges in solution were shaken at 125 rpm overnight. The sponges were removed and the absorption spectrum of the solution was taken to measure the amount of chlorhexidine removed from the solution by the sponges. The reactive dyes are described more fully in "The Chemistry of Synthetic Dyes", Volume VI (Academic Press, 1972), incorporated herein by reference

TABLE I

| Compound name | Total uptake (μg)/sponge |
| --- | --- |
| 1) blank sponge | 104 |
| 2) Cibacron Orange FR | 10227 |
| 3) Cibacron Scarlet FR | 16749 |
| 4) Cibacron Blue | 3072 |
| 5) Cibacron Navy FG | 6273 |
| 6) Cibacron Yellow F-4G | 3779 |
| 7) Cibacron Blue FR | 3470 |
| 8) Cibacron Yellow F3R | 9313 |
| 9) Cibacron Red FB | 2703 |
| 10) Cibacron Brill. Red 3BA | 1460 |
| 11) Cibacron Yellow CR01 | 5865 |
| 12) Cibacron Navy CB | 4860 |
| 13) Cibacron Yellow C5G | 2332 |
| 14) Cibacron Blue CR | 3080 |
| 15) Cibacron Red C2G | 4913 |
| 16) Cibacron Brill. Yellow 3G | 1405 |
| 17) Cibacron Orange CG | 5672 |
| 18) Ramazol Yellow Green | 2056 |
| 19) Ramazol Turquoise | 469 |
| 20) Ramazol Brill. Blue | 1012 |
| 21) Ramazol Blue Black | 5235 |
| 22) Ramazol Red | 2495 |
| 23) Reactive Orange 16 | 2635 |
| 24) Reactive Blue 4 | 2124 |

The foregoing reactive dyes referred to in this embodiment are, of course, colored compounds which impart color to the cellulosic material. In some instances, it may be preferable to employ a compound which possesses the scavenging characteristics and yet is uncolored. Thus, an uncolored compound of the formula

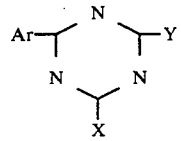

wherein
Ar is an aromatic group bound to the triazinyl ring through a bridging group said aromatic group containing at least one sulfonic acid group
X is chlorine or fluorine, and
Y is chlorine, fluorine or Ar can be employed to react with the cellulosic material to form the scavenger element. One specific compound which can be employed is

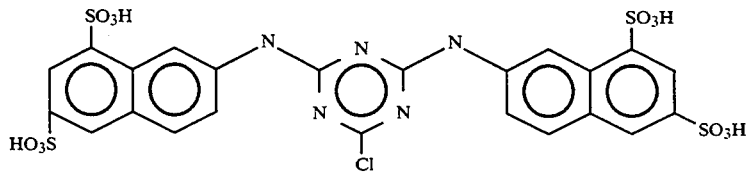

In accordance with the method described above, this compund was found to have an uptake of 2546 μg/sponge.

Having described the invention, what is claimed is:

1. A method for the sterilization or disinfection of an object in need of such treatment, which comprises immersing an object in a sterilizing or disinfecting solution containing an antimicrobial effective amount of at least one cationic or at least one anionic antimicrobial agent in the presence of a solid scavenger element containing a scavenger material which is selected from the group consisting of a cationic exchange resin and an anionic exchange resin and which, over a period of time, sufficiently removes from said solution said cationic or anionic antimicrobial agent at a rate permitting sterilization or disinfection of the said object and which prevents undesirable build-up of the antimicrobial agent in or on the said object, allowing said object to remain in said solution for at least a period of time sufficient for said scavenger element to remove from the said solution a sufficient amount of the antimicrobial agent to render said object safe for use for its intended purpose and removing said object from said solution.

2. A method according to claim 1 wherein the object to be sterilized or disinfected is a contact lens.

3. A method according to claim 2 wherein said contact lens is a soft hydrogel contact lens.

4. A method according to claim 3 wherein the said contact lens is permitted to remain in said solution for at least 30 minutes.

5. A method according to claim 4 wherein the said contact lens is permitted to remain in the said solution for a period of time sufficient to achieve complete sterilization or disinfection of said lens.

6. A method according to claim 5 wherein the period of time is about 4 hours.

7. A method according to claim 4 wherein the contact lens is permitted to remain in the solution for up to 30 days.

8. A method according to claim 1 wherein the antimicrobial effective amount of antimicrobial agent is about 50 to about 100 parts per one million parts by weight of solution.

9. A method according to claim 8 wherein the said amount is about 50 ppm and the scavenging rate of the scavenger material is such that after about 30 minutes contact time between the scavenger element and the solution, the solution contains about 30 ppm of antimicrobial agent.

10. A method according to claim 9 wherein after about one hour contact time the solution contains about 10 ppm of antimicrobial agent.

11. The method of claim 1, wherein the scavenger element is a substrate dyed with a reactive dye containing at least one sulfonic acid group.

12. The method of claim 11, wherein the scavenger element is a cellulosic material.

13. The method of claim 12, wherein the cellulosic material is a sponge.

14. The method of claim 11, wherein the reactive dye has the formula.

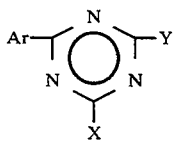

wherein P1 Ar is an aromatic bound to the triazinyl ring through a bridging group said aromatic group containing at least one sulfonic group X is chlorine or fluorine, and Y is chlorine, fluorine or Ar.

15. A container for sterilizing or disinfecting an object in need of such treatment which comprises a main body portion defining a reservoir capable of receiving an object to be sterilized or disinfected and a sufficient amount of an antimicrobial solution containing a positively or negatively charged antimicrobial agent in which to immerse said object, a solid scavenger element positioned within said reservoir in a manner to permit contact with said antimicrobial solution, said scavenger element containing a scavenger material selected from the group consisting of a cationic exchange resin and an anionic exchange resin, which scavenger element, over a period of time, sufficiently removes from said antimicrobial solution said positively or negatively charged antimicrobial agent at a rate permitting sterilization or disinfection of said object and which prevents undesirable build-up of the antimicrobial agent in or on said object, and a top closure for sealing the main body.

16. A container according to claim 15 for the sterilization or disinfection of contact lenses wherein said main body portion contains a contact lens holder within said reservoir, said contact lens holder being configured to receive at least one contact lens and to suspend said lens within said reservoir.

17. A container according to claim 16 wherein said contact lens holder is porous thereby permitting circulation of an antimicrobial solution therethrough.

18. A container according to claim 16 wherein the main body portion defines two separate and discrete reservoirs each of which is adapted to receive one contact lens.

19. A container according to claim 15 wherein at least the main body portion is formed from a material which will perform the scavenging function.

20. A container according to claim 15 wherein said scavenger element is in the form of a disc having cutaway portions to form essentially equispaced radial arms.

21. A container according to claim 15 wherein the interior portions of the main body forming the reservoir are coated with a scavenging material to form the scavenger.

22. A container according to claim 15 wherein said scavenger element comprises a synthetic resin and said cationic or anionic exchange resin.

23. A container according to claim 15 wherein said scavenger element is in the form of a membrane.

24. A container according to claim 15 wherein said scavenger element comprises a paper material containing a cationic or anionic exchange resin.

25. A container according to claim 15 wherein top said closure is a screw top.

26. A container according to claim 15 wherein said top closure is a top adapted to snap-fit on said main body portion.

* * * * *